United States Patent
Chen et al.

(10) Patent No.: US 9,510,760 B2
(45) Date of Patent: Dec. 6, 2016

(54) METHOD FOR ESTIMATING CENTRAL AORTIC PULSE PRESSURE BY CUFF PRESSURE PULSE WAVE OSCILLATION SIGNALS AND DEVICE THEREOF

(71) Applicant: NATIONAL YANG-MING UNIVERSITY, Taipei (TW)

(72) Inventors: Chen-Huan Chen, Taipei (TW); Hao-Min Cheng, Taipei (TW); Shih-Hsien Sung, Taipei (TW)

(73) Assignee: National Yang-Ming University, Taipei (TW)

( * ) Notice: Subject to any disclaimer, the term of this patent is extended or adjusted under 35 U.S.C. 154(b) by 648 days.

(21) Appl. No.: 13/714,058

(22) Filed: Dec. 13, 2012

(65) Prior Publication Data

US 2013/0345576 A1 Dec. 26, 2013

(30) Foreign Application Priority Data

Jun. 20, 2012 (TW) .............................. 101122117 A

(51) Int. Cl.
   *A61B 5/02* (2006.01)
   *A61B 5/022* (2006.01)

(52) U.S. Cl.
   CPC ................. *A61B 5/02225* (2013.01)

(58) Field of Classification Search
   CPC ..... A61B 5/022; A61B 5/021; A61B 5/0225
   See application file for complete search history.

(56) References Cited

U.S. PATENT DOCUMENTS

| | | | |
|---|---|---|---|
| 6,511,436 B1* | 1/2003 | Asmar | A61B 5/021 600/481 |
| 2006/0041281 A1* | 2/2006 | Von Arx et al. | 607/18 |
| 2007/0185400 A1* | 8/2007 | O'Rourke | 600/485 |
| 2009/0149763 A1* | 6/2009 | Chen et al. | 600/494 |
| 2009/0312653 A1* | 12/2009 | Sharrock et al. | 600/495 |
| 2011/0275944 A1* | 11/2011 | Qasem | 600/493 |

OTHER PUBLICATIONS

Cheng, H., Wang, K., Chen, Y., Lin, S., Chen, L., Sung, S., Ding, Y., Yu, W., Chen, J.,Chen, C. (2010). Estimation of central systolic blood pressure using an oscillometric blood pressure monitor. Hypertens Res Hypertension Research, 592-599. Retrieved May 29, 2015, from http://www.ncbi.nlm.nih.gov/pubmed/20339373.*
Wilkinson, I., Mohammad, N., Tyrrell, S., Hall, I., Webb, D., Paul, V., Levy, T., Cockcroft, J. (2002). Heart rate dependency of pulse pressure amplification and arterial stiffness. American Journal of Hypertension, 24-30. Retrieved May 29, 2015, from http://www.ncbi.nlm.nih.gov/pubmed/11824855.*
Williams, B., Lacy, P., Yan, P., Hwee, C., Liang, C., Ting, C. (2011) Development and validation of a novel method to derive central aortic systolic pressure from the radial pressure waveform using an N-point moving average method. Journal of the Americal College of Cardiology, 57, 8: 951-61. Retrieved May 29, 2015 from PubMed.*
Waner, Stefan. "Linear and Exponential Regression." Linear and Exponential Regression. N.p., Jan. 2008. Web. Jun. 12, 2015. <http://www.zweigmedia.com/RealWorld/calctopic1/regression.html>.*

* cited by examiner

Primary Examiner — Jacqueline Cheng
Assistant Examiner — Lauren Querido
(74) Attorney, Agent, or Firm — Hannah M. Tien

(57) ABSTRACT

A method and device for estimating central aortic pulse pressure by cuff pressure pulse wave oscillation signals. The method comprises (I) providing an equation for estimating central aortic pulse pressure; (II) measuring pressure pulse wave oscillation signals in a cuff, which comprise a brachial systolic blood pressure, a diastolic blood pressure and a waveform of the pressure pulse wave oscillation signals in the cuff; (III) averaging the waveform of the pressure pulse wave oscillation signals and calibrating the averaged waveform; (IV) analyzing the calibrated pressure pulse wave oscillation signal waveform to obtain a plurality of predicting variables; and (V) obtaining an estimate of the central aortic pulse pressure by values of predicting variables in step (IV) and the equation in step (I).

6 Claims, 7 Drawing Sheets

| Blood pressure variable (mmHg) | Generation Group (n=80) | | | | | | Validation Group (n=200) | | | | | |
|---|---|---|---|---|---|---|---|---|---|---|---|---|
| | Baseline (n=40) | | | After NTG (n=40) | | | Baseline (n=100) | | | After NTG (n=100) | | |
| | Mean±SD | p-value of differences | R value | Mean±SD | p-value of differences | R value | Mean±SD | p-value of differences | R value | Mean±SD | p-value of differences | R value |
| Cuff PP | -4.9 ±9.7** | 0.0024 | 0.86** | 5.8 ±8.0** | <0.0001 | 0.82** | -4.5 ±9.4** | <0.0001 | 0.84** | 8.0 ±12.0** | 0.0000 | 0.55** |
| PP-C$_{TFSBP-TFDBP}$ | -9.6 ± 8.4** | <0.0001 | 0.90** | 0.5 ± 8.1 | 0.7073 | 0.82** | -8.9 ±8.6** | <0.0001 | 0.87** | 2.0 ± 11.6 | 0.0829 | 0.58** |
| PP-C$_{TFSBP-CUFFDBP}$ | -9.3 ± 8.3** | <0.0001 | 0.90** | 0.9 ± 8.3 | 0.5202 | 0.81** | -7.6 ±8.5** | <0.0001 | 0.87** | 3.0 ± 11.6 | 0.0115 | 0.58** |
| PP-C$_{PWASBP-CUFFDBP}$ | -8.5 ± 7.0** | <0.0001 | 0.93** | -3.7 ±6.7* | 0.0013 | 0.88** | -5.7 ±7.2** | <0.0001 | 0.91** | -1.9 ± 7.4 | 0.0119 | 0.87** |

*FIG. 4*

FIG. 5(A)
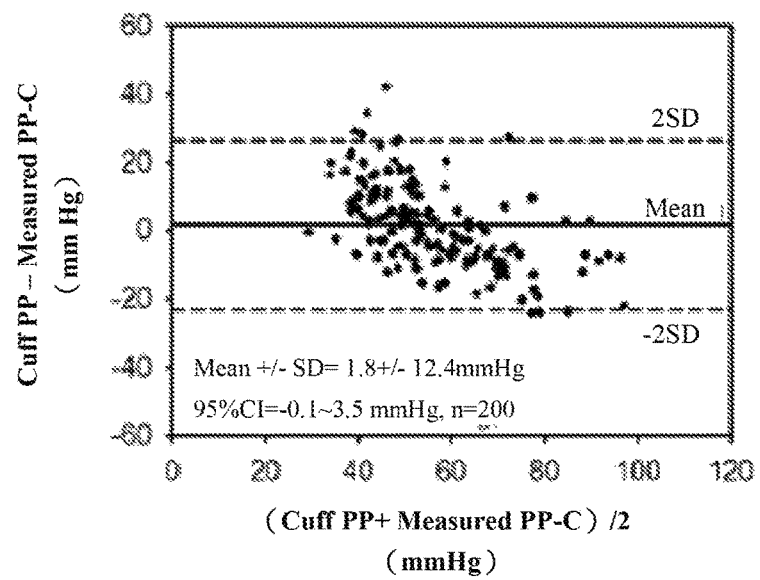
FIG. 5(B)
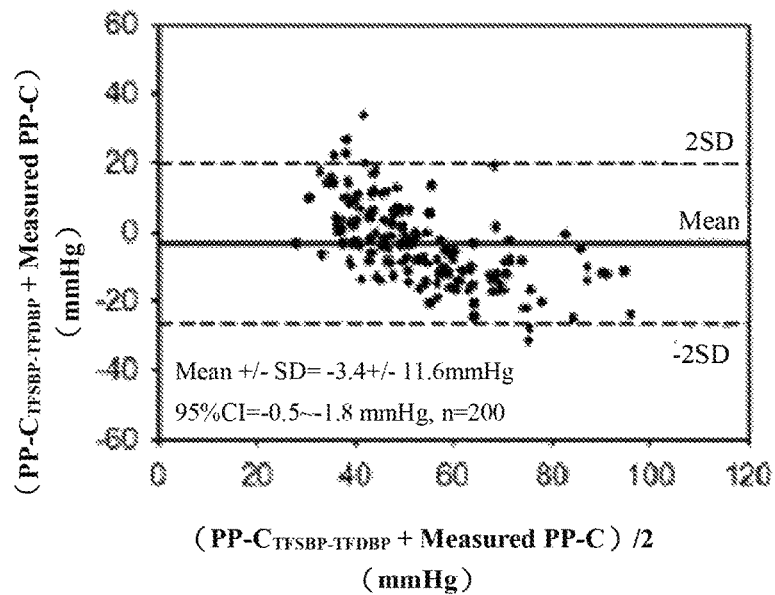
FIG. 5

FIG. 5(C)
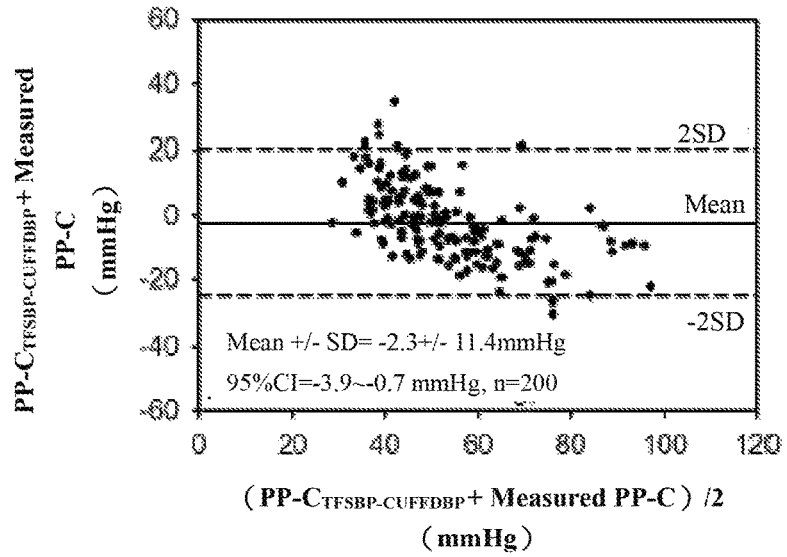
FIG. 5(D)
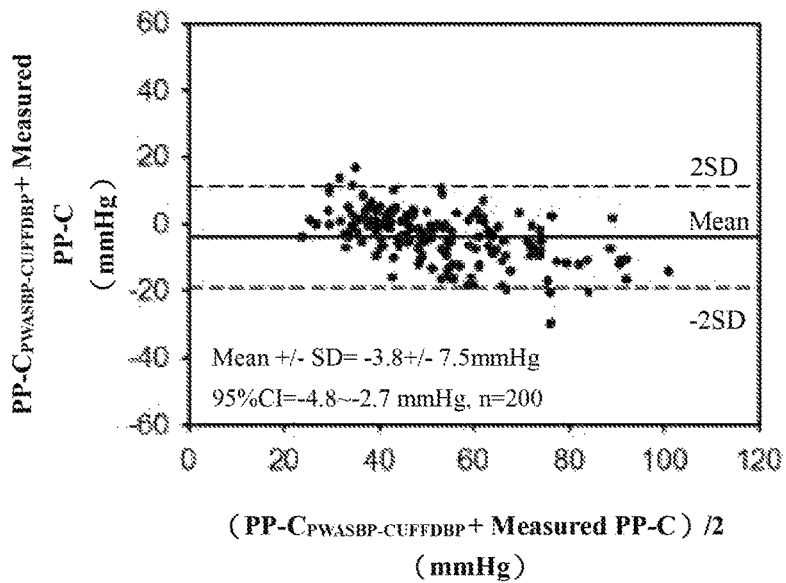
FIG. 5

FIG. 6(A)
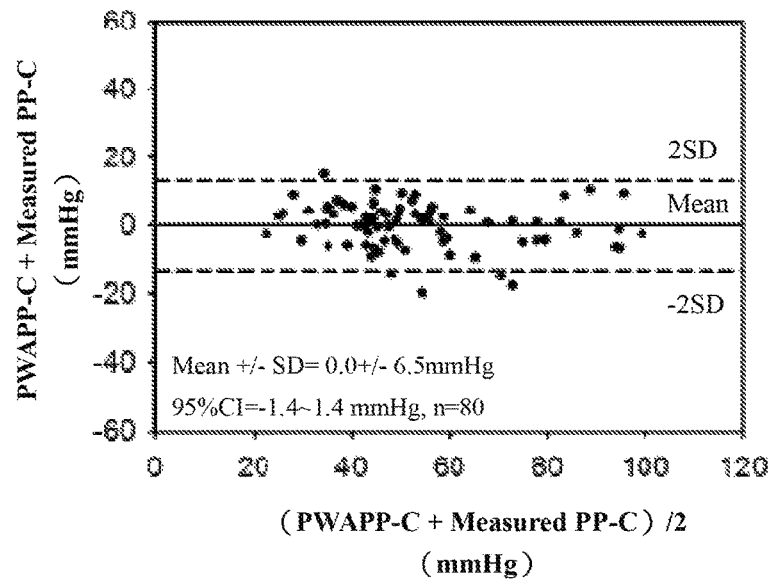
FIG. 6(B)
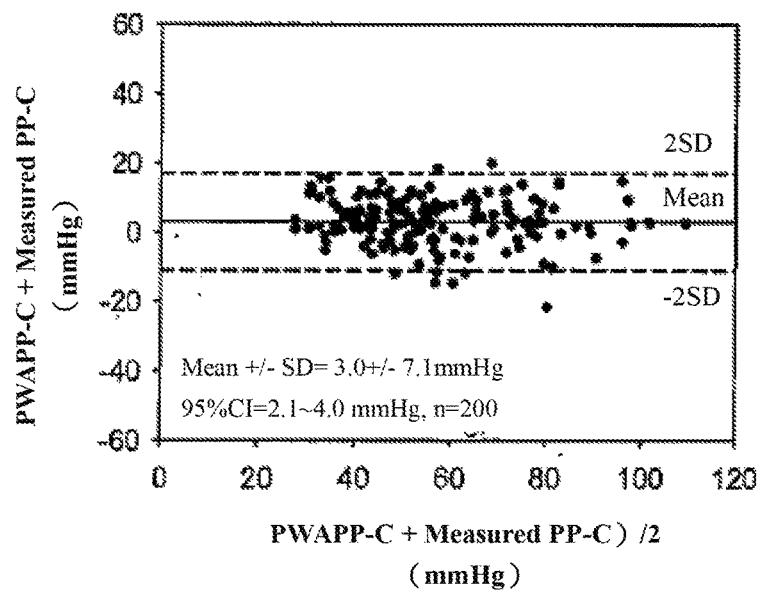
FIG. 6

METHOD FOR ESTIMATING CENTRAL AORTIC PULSE PRESSURE BY CUFF PRESSURE PULSE WAVE OSCILLATION SIGNALS AND DEVICE THEREOF

FIELD OF THE INVENTION

The present invention relates to a method for estimating a central aortic pulse pressure by cuff pressure pulse wave oscillation signals and device thereof.

DESCRIPTION OF PRIOR ART

The feature of an arterial hypertension is that increase of peripheral vascular resistance that results in enhancing obstacle to blood flow at the arteriole and elevating the mean blood pressure. The diagnosis of hypertension is based on the measured value of brachial systolic blood pressure or diastolic blood pressure by traditional mercury or an electronic sphygmomanometer, and the pulse pressure is calculated as the difference between the systolic blood pressure and the diastolic blood pressure. The ventricular stroke volume and the arterial compliance, which reflects the degree of arteriosclerosis, are two main factors to determine the pulse pressure. Thus, the value of the pulse pressure is capable of representing the arterial stiffness and aging. In the past, the study showed that the pulse pressure of brachial artery was more capable of predicting risk for future cardiovascular disease than that of the mean blood pressure. In addition, the waveform and blood pressure of the brachial artery are influenced by the arterial stiffness and the reflected wave in upper arms, and therefore could not represent those of the central artery. Many epidemiologic studies and clinical drug trials verified that it has higher value in clinical application for systolic blood pressure and diastolic blood pressure of the central artery than that of the peripheral artery. In particular, the central pulse pressure is deemed as an effective mechanical biomarker.

Pulse pressure is calculated by deducting the diastolic blood pressure from the systolic blood pressure; however the accuracy of the pulse pressure was influenced by both the measurement inaccuracy for the systolic blood pressure and the diastolic blood pressure. In the past, the study showed that in general, the brachial systolic blood pressure measured by an electronic sphygmomanometer is slightly lower than the systolic blood pressure measured directly with invasive cardiac catheterization, and the brachial diastolic blood pressure is significantly higher than that measured directly by the cardiac catheterization, while it also exhibits a obvious systematic bias, which means that when the blood pressure is higher, the diastolic blood pressure measured by the electronic sphygmomanometer will possibly underestimate the invasively measured diastolic blood pressure. However, when the blood pressure is lower, the diastolic blood pressure measured with the electronic sphygmomanometer will possibly overestimate the invasively measured diastolic blood pressure. Thus, the inaccuracy of the diastolic blood pressure will produce inaccurate pulse pressure inevitably.

Currently, there are some non-invasive methods for estimating the central aortic systolic blood pressure and the central aortic diastolic blood pressure. However, a commonality of these methods is to use an arterial tonometer first to obtain the pressure waveform of the radial artery or the carotid artery, and then to use the electronic sphygmomanometer to measure the systolic blood pressure and the diastolic blood pressure or the diastolic blood pressure and the mean blood pressure for the calibration of the arterial pressure waveform. Because the diastolic blood pressure measured by the electronic sphygmomanometer exhibits considerable inaccuracy and obvious systematic bias, these errors are transferred to a final estimated value of the central aortic diastolic blood pressure through a procedure of calibration of the pressure waveform, and the calculated central aortic pulse pressure also inherits the inaccuracy and systematic bias of the diastolic blood pressure measured by the electronic sphygmomanometer.

Currently, the non-invasive methods for calculating the central aortic pulse pressure comprising two types:

The first type: using a pen-shaped arterial tonometer to obtain the pressure waveform of the radial artery, and at the same time, using the general electronic sphygmomanometer to measure the systolic blood pressure and the diastolic blood pressure of the brachial artery, thereby calibrating the pressure waveform of the radial artery. Then, the calibrated pressure waveform of the radial artery is reconstructed to a pressure waveform of the ascending aorta with a known mathematical transfer function, and the reconstructed pressure waveform of the ascending aorta is used to estimate the systolic blood pressure and the diastolic blood pressure directly and calculate the pulse pressure. The above technology has been commercialized; however, this product must equip with an expensive pen-shaped arterial tonometer and an exclusive notebook. In addition, the pen-shaped arterial tonometer has a threshold in operation that affects the accuracy of the estimated value.

Moreover, another limitation of this technology is that the mathematical transfer function that does not overcome the inaccuracy and the systematic bias from the diastolic blood pressure of the brachial artery measured by the electronic sphygmomanometer. Thus, the accuracy of the estimated central aortic pulse pressure is decreased.

The second type: adopting other methods for estimating the central aortic systolic blood pressure. Users treat the diastolic blood pressure of brachial artery measured by the general tonometer as the central aortic diastolic blood pressure. Then, the central aortic pulse pressure mentioned above is derived by subtracting the diastolic blood pressure of brachial artery from the central aortic systolic blood pressure. However, the inaccuracy and the systematic bias from diastolic blood pressure of the brachial artery measured by the electronic sphygmomanometer are entirely introduced into the calculated central aortic pulse pressure by using this calculating method, such as commercial pressure recorder apparatus with wrist-type or watch-type (HEM-9000AI) and the electronic sphygmomanometer that uses a similar mathematical transfer function and reconstructs a waveform of the ascending aorta by the cuff pressure pulse wave oscillation signals, thereby estimating the central aortic systolic blood pressure.

BRIEF DESCRIPTION OF THE DRAWINGS

FIG. 4 shows comparisons of cuff PP and various noninvasive estimates of PP-C with the invasively measured PP-C.

Figure 1:
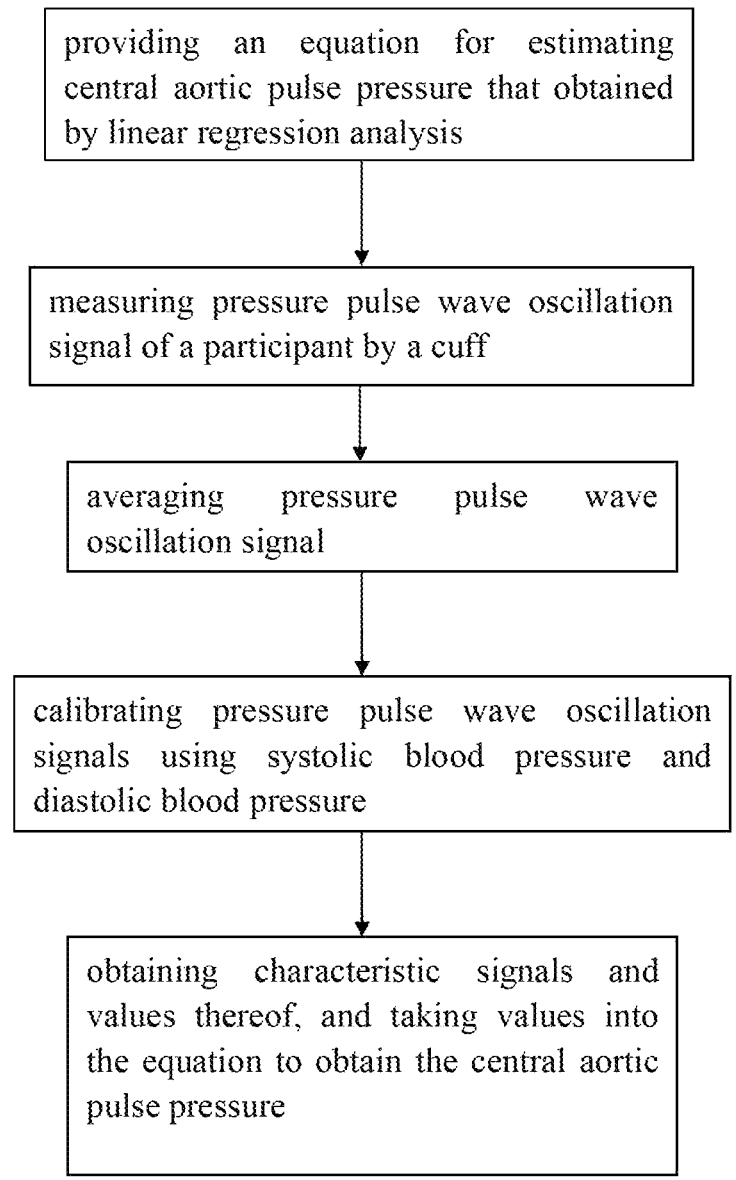
FIG. 1 is a block chart of the present invention for estimating a central aortic pulse pressure.

Cuff PP represents measuring pulse pressure of brachial artery by cuff; PP-C TFSBP-TFDBP represents the central aortic pulse pressure=reconstructed aortic SBP by generalized transfer function (TFSBP)-reconstructed aortic DBP by generalized transfer function (TFDBP); PP-C$_{TFSBP-CUFFDBP}$ represents the central aortic pulse pressure=reconstructed aortic SBP by generalized transfer function (TFSBP)-Cuff DBP; PP-C$_{PWASBP-CUFFDBP}$ represents the central aortic pulse pressure=estimated aortic SBP by a pulse wave analysis method (PWASBP)-Cuff DBP.

FIG. 5 shows results of combined measurements using various blood pressure value and invasive central aortic pulse pressure via the Bland-Altman analysis at a baseline and after administration of nitroglycerin.

SBP-C represents central aortic systolic blood pressure; PP-C represents central aortic pulse pressure; and GTF represents the generalized transfer function.

FIG. 5(A) shows accuracy with respect to the measured central aortic pulse pressure (PP-C) by the non-invasive method and the measured central aortic pulse pressure by a cuff (Cuff-PP) in the Validation Group.

FIG. 5(B) and FIG. 5(C) show that the pulse pressure is calculated by the generalized transfer function (GTF) approach, such as the accuracy for PP-C$_{TFSBP-TFDBP}$ and PP-C$_{TFSBP-Cuff\,DBP}$.

PP-C$_{TFSBP-TFDBP}$ represents central aortic pulse pressure=reconstructed aortic SBP by generalized transfer function (TFSBP)-reconstructed aortic DBP by generalized transfer function (TFDBP); and PP-C$_{TFSBP-CUFFDBP}$ represents central aortic pulse pressure=reconstructed aortic SBP by generalized transfer function (TFSBP)-Cuff DBP.

FIG. 5(D) shows accuracy of using PWA approach to obtain the estimated value of the central systolic blood pressure and using cuff diastolic blood pressure to calculate the central aortic pulse pressure.

FIG. 6 is a comparison of the central aortic pulse pressure between using a pulse volume plethysmography (PVP) and using an invasive method.

FIG. 6(A) represents the Generation Group; and FIG. 6(B) represents the Validation Group.

SUMMARY OF THE INVENTION

The present invention provides a method for estimating central aortic pulse pressure by a pressure pulse wave oscillation signal of a cuff, comprising: (I) providing an equation for estimating a central aortic pulse pressure; (II) measuring the pressure pulse wave oscillation signal in the cuff, comprising a brachial systolic blood pressure, a diastolic blood pressure and a waveform of the pressure pulse wave oscillation signals in the cuff; (III) averaging the waveform of the pressure pulse wave oscillation signal and calibrating the averaged waveform by the systolic blood pressure and the diastolic blood pressure; (IV) analyzing the calibrated waveform of the pressure pulse wave oscillation signals to obtain a plurality of characteristic signal values, in which a characteristic signal serves as a predicting variable, and predicting variables comprising: (a) end-systolic pressure (ESP), (b) areas under a pressure tracing in systole (As), (c) areas under a pressure tracing in diastole (Ad), (d) diastolic blood pressure (DBP) and (e) heart rate (HR); and (obtaining an estimate of the central aortic pulse pressure by substituting values of the predicting variables of step (IV) into the equation of step (I).

The present invention further provides a device for estimating central aortic pulse pressure by a pressure pulse wave oscillation signal of a cuff, comprising: (a) means for regulating a pressure of the cuff, which is used to control the proceeding of pressurization, maintenance and decompression in a measured location of the cuff; (b) means for recording and storing the pressure pulse wave oscillation signal of the cuff; and (c) means for analyzing the central aortic pulse pressure, comprising storing means for storing a equation for estimating the central aortic pulse pressure to calculate in real-time an estimate of the central aortic pulse pressure by a value of a predicting variable, wherein the equation comprises a plurality of the predicting variables and predicting coefficients, and wherein the predicting variables comprise (a) end-systolic pressure (ESP), (b) areas under a pressure tracing in systole (As), (c) areas under a pressure tracing in diastole (Ad), (d) diastolic blood pressure (DBP) and (e) heart rate (HR).

DETAILED DESCRIPTION OF THE INVENTION

The present invention is related to an improved method for analyzing a pulse wave, in which a multi-variate prediction model is constructed with the calibrated waveform of the pressure pulse wave oscillation signals, and an equation is produced for estimating central aortic pulse pressure directly. In addition, an user is capable of using the present method to develop a novel manometer with improved accuracy. The novel manometer does not need to be equipped with expensive pen-shaped arterial tonometer and a companion laptop, while the operation thereof is the same as the general manometer.

As mentioned above, the present invention provides a method for estimating central aortic pulse pressure in real-time by a pressure pulse wave oscillation signal of a cuff. As shown in FIG. 1, the method comprises (I) providing an equation for estimating a central aortic pulse pressure; (II) measuring the pressure pulse wave oscillation signal in the cuff, comprising a brachial systolic blood pressure, a diastolic blood pressure and a waveform of pressure pulse wave oscillation signals in the cuff; (III) averaging the waveform of the pressure pulse wave oscillation signals and calibrating the averaged waveform by the systolic blood pressure and the diastolic blood pressure; (IV) analyzing the calibrated waveform of the pressure pulse wave oscillation signals to obtain a plurality of characteristic signal values, in which a characteristic signal serves as a predicting variable, and the predicting variables comprise: (a) end-systolic pressure (ESP), (b) areas under a pressure tracing in systole (As), (c) areas under a pressure tracing in diastole (Ad), (d) diastolic blood pressure (DBP) and (e) heart rate (HR); and (obtaining an estimate of the central aortic pulse pressure by substituting values of the predicting variables of step (IV) into the equation of step (I).

In one embodiment of the present invention, the equation for estimating central aortic pulse pressure obtains a plurality of the predicting variables and the predicting coefficients by linear regression analysis, wherein the equation for estimating the central aortic pulse pressure is: a+b*ESP+c*As+d*Ad+e*DBP+f*HR. In a preferred embodiment, the equation for estimating the central aortic pulse pressure is: −88.2+0.79*ESP+1.41*As+0.68*Ad−1.16*DBP+0.84*HR. In the equation, a is a constant and the predicting coefficients of b, c, d, e and f are variable coefficients obtained from Stepwise linear regression analysis.

In one embodiment of the present invention, the recited "central artery" in the present invention comprises in definition carotid artery or ascending aorta, and "pulse pressure" is an estimating aim by using the non-invasive method of the present invention. The signal in the cuff is a signal from brachial artery.

The present invention further provides a novel electronic sphygmomanometer for estimating central aortic pulse pressure by a pressure pulse wave oscillation signal of a cuff, comprising: (a) a control means for controlling a pressure of the cuff, which is used to control the proceeding of pressurization, maintenance and decompression in a measured location of the cuff; (b) a recording means for recording and storing the pressure pulse wave oscillation signal of the cuff; and (c) a processing means for estimating the central aortic pulse pressure, comprising storing means for storing an equation for estimating the central aortic pulse pressure to calculate in real time an estimate of the central aortic pulse pressure by values of a plurality of predicting variables, wherein the equation comprises the plurality of the predicting variables and predicting coefficients, and wherein the predicting variables comprise (a) end-systolic pressure (ESP), (b) areas under a pressure tracing in systole (As), (c) areas under a pressure tracing in diastole (Ad), (d) diastolic blood pressure (DBP) and (e) heart rate (HR).

In one embodiment of the present invention, the equation for estimating the central aortic pulse pressure obtains a plurality of the predicting variables and predicting coefficients by linear regression analysis, wherein the equation for estimating the central aortic pulse pressure is: $a+b*ESP+c*As+d*Ad+e*DBP+f*HR$, wherein a is a constant and the predicting coefficients of b, c, d, e and f are variable coefficients obtained from Stepwise linear regression analysis. In a preferred embodiment, the equation for estimating the central aortic pulse pressure is: $-88.2+0.79*ESP+1.41*As+0.68*Ad-1.16*DBP+0.84*HR$.

In one embodiment of the present invention, the location measured by means for regulating a pressure in the cuff is brachial artery.

In one embodiment of the present invention, the storing means is a chip or a memory storage device.

The term "waveform of the pressure pulse wave oscillation" used herein, unless otherwise indicated, means pulse volume plethysmography (PVP) of brachial artery.

In this application, certain terms are used, which shall have the meanings as set in the specification. It must be noted that as used herein and in the appended claims, the singular forms "a," "an," and "the" include plural reference unless the context clearly dictates otherwise. Unless defined otherwise, all technical and scientific terms used herein have the same meaning as commonly understood to one with ordinary skill in the art to which this invention pertains.

EXAMPLES

The examples below are non-limiting and are merely representative of various aspects and features of the present invention.

Example

Establishing an Equation for Estimating the Central Aortic Pulse Pressure, and Comparing the Established Method with Other Methods for Calculating the Central Aortic Pulse Pressure Group Study and Signal Acquisition Process Subjects under test (or abbreviated "subjects" hereinafter) were divided into two groups, one group was a Generation Group, and the other group was a Validation Group. In the present example, subjects received catheterization through the radial artery to examine coronary anatomy. Subjects with acute coronary syndrome and peripheral arterial disease were excluded. In addition, subjects with rhythms other than normal sinus rhythm and having more than 3 mmHg pressure difference between left and right arms were also excluded.

The standard of the central aortic pulse pressure generally adopted a cardiac catheterization technology to obtain an invasive central aortic blood pressure. The present example also adopted the same standard to verify the accuracy of the present invention.

Signal Acquisition Proceeding in the Generation Group

First, 40 subjects were recruited. Then a first sensor and a second sensor of a custom-designed 2F dual-sensor high-fidelity micromanometer-tipped catheter (model SPC-320, Millar Instrument Inc., USA) were placed respectively at the ascending aorta and the right brachial artery in each subject, thereby simultaneously recording waveforms of the blood pressure of the brachial artery and the aorta in an invasive manner. On the other hand, the systolic blood pressure and diastolic blood pressure of the subject's left arm were measured by an oscillometric manometer (WatchBP Office, Microlife AG, Widnau, Switzerland), while simultaneously recording the pulse volume plethysmography (PVP) at a mean cuff pressure of 60 mmHg for 30 seconds.

Signal Acquisition Proceeding in the Validation Group

The custom-designed 2F dual-sensor high-fidelity micromanometer-tipped catheter (model SPC-320, Millar Instrument Inc., USA) and an oscillometric manometer (VP-2000, Colin Corporation, Komaki, Japan) were used to record the central aortic pressure and left-arm PVP waveform for 100 subjects at the mean cuff pressure of 60 mmHg for 30 seconds.

Each subject accepted two measurements, comprising the baseline and 3 minutes after administration of a sublingual nitroglycerin (NTG), and all waveforms of signals were recorded.

Data Analysis and Calculation Method

After recording of data of the two groups, the waveforms of the central aortic pressure and pulse volume plethysmograpy (PVP) in the upper arm were obtained, and then further 20 beats waveform signals were retrieved to average the waveform. The central aortic systolic blood pressure and the central aortic diastolic blood pressure were estimated respectively by a high peak point of the averaged waveform of the central aortic pressure and the end-diastole, respectively. Finally, the difference value of the central aortic systolic blood pressure and the central aortic diastolic blood pressure was the invasive central aortic pulse pressure.

The Present Invention: Constructing a Method for Estimating Central Aortic Pulse Pressure After averaging the waveform of the pressure pulse wave oscillation signal, the averaged waveform was calibrated by the systolic blood pressure and diastolic blood pressure of the brachial artery measured by the electronic sphygmomanometer, then the waveform was analyzed to find the characteristic signal (characteristic point), and finally, the best predicting variables (characteristic point) were determined by the Stepwise linear regression analysis, thereby obtaining the coefficients of predicting variable from the equation.

Figure 2:
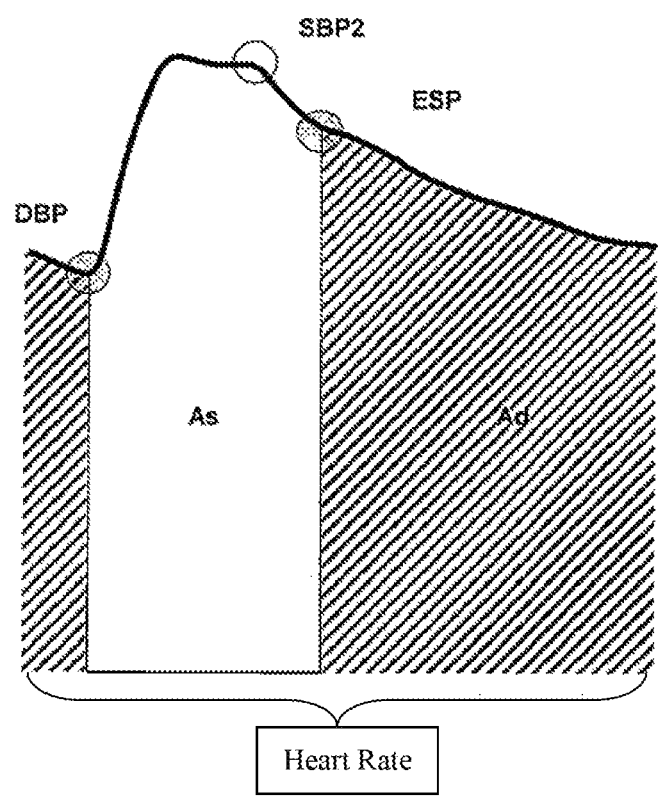
FIG. 2 is a schematic drawing of a pulse wave oscillation waveform comprising characteristic points (DBP represents diastolic blood pressure; SBP2 represents secondary peak systolic pressure; ESP represents end-systolic pressure; As represents areas under a pressure tracing in systole; and Ad represents areas under a pressure tracing in diastole).

In the present example, the above characteristic points of PVP waveform were measured by an automatic analysis technology (Matlab®, version 4.2, The Math works, Inc.) to avoid the selection bias. As shown in FIG. 2, these predicting variables of waveform (characteristic points) comprised diastolic blood pressure (DBP), secondary peak systolic pressure (SBP2), areas under the pressure tracing in systole (As), areas under the pressure tracing in diastole (Ad), end-systolic pressure (ESP) and heart rate.

Other Methods for Calculating the Central Aortic Pulse Pressure: The Generalized Transfer Function (GTF) and the Pulse Wave Analysis (PWA)

1. Generalized Transfer Function (GTF)

Figure 3:
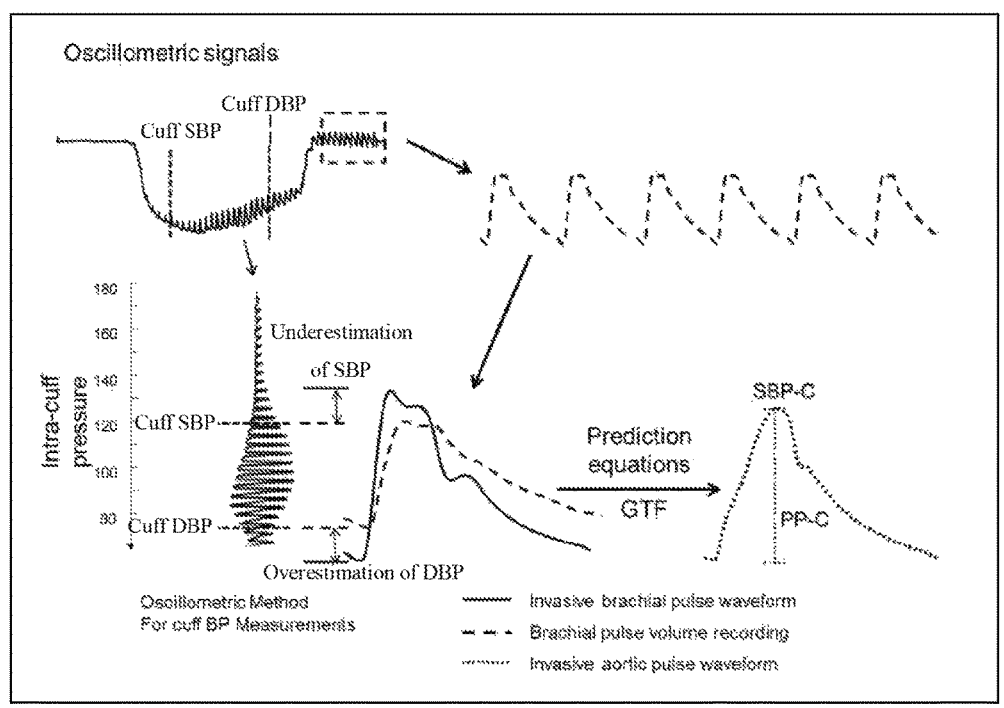
FIG. 3 shows various methods for estimating central aortic pulse pressure.

Currently, there were many methods to obtain the central aortic blood pressure by the non-invasive method. The first method was to transform the pressure waveform of peripheral artery (such as radial artery or brachial artery) by using the Generalized Transfer Function so as to reconstruct the waveform of the central aortic pulse pressure. FIG. 3 showed the process. The calibrated PVP reconstructed the pulse wave of the aorta by the Generalized Transfer Function, and then the values of the central aortic systolic blood pressure (SBP-C) and the central aortic diastolic blood pressure (DBP-C) were obtained. The second method was to ignore the inaccuracy of the general electronic sphygmomanometer, and treat the cuff diastolic blood pressure as the central aortic diastole blood pressure. The above methods for calculating the central aortic pulse pressure as following formula:

The first method: $PP\text{-}C_{TFSBP\text{-}TFDBP} = GTF_{SBP} - GTF_{DBP}$.

The second method: $PP\text{-}C_{TFSBP\text{-}Cuff\ DBP} = GTF_{SBP} - Cuff_{DBP}$.

2. Pulse Wave Analysis (PWA)

Previous study disclosed using the cuff pulse wave analysis method with a multi-variate prediction model (cuff-based PWA) for estimating the central aortic pulse pressure. The pulse volume plethysmography (PVP) was used for identifying some parameters related to the wave reflection and the arterial compliance through an automatic waveform analysis technology. In the multi-variate model, various waveform parameters comprised the secondary peak systolic pressure (SBP2) caused by wave reflection, areas under the pressure tracing in diastole (Ad) and areas under the pressure tracing in systole (As). In addition, the value of SBP2 was related to the intensity of pressure wave reflection, and ESP, Ad and As were related to the arterial compliance. Previous study verified that using the above method to estimate the central aortic systolic blood pressure (SBP-C) had acceptable accuracy. The formula for calculating the central aortic pulse pressure was as follows:

The third method: $PP\text{-}C_{PWASBP\text{-}Cuff\ DBP} = PWASBP - Cuff\ DBP$.

Statistics Analysis:

In the present example, all the baseline data were tested normality by a Shapiro-Wilk test, and comparisons of paired blood pressure values and differences thereof were executed by a paired student t test or paired-sample Wilcoxon signed rank test (non-parametric test). All variables comprising waveform parameter in the multi-variate model were normally distributed. In addition, the present example provided that the conformity evaluation for the waveform characteristic point in PVP, the estimated values obtained from the estimated equation and the pulse pressure obtained from the cardiac catheterization. The evaluation parameters comprised mean difference and standard deviation of difference, and comparisons of the evaluation index were executed by the Bland-Altman analysis approach. Statistical difference was indicated by the two-tailed P<0.05 or attended by Bonferroni correction.

Result:

Other Method for Calculating Central Aortic Pulse Pressure

As shown in FIG. 4, in the Generation Group and the Validation Group, the subjects without administrating nitroglycerin (NTG) were treated as "Baseline", in which the pulse pressure was measured by the cuff that underestimated the central aortic pulse pressure by the non-invasive method at "Baseline". Meanwhile, the subjects with administrating nitroglycerin (NTG) were treated as "after NTG", in which the pulse pressure was measured by the cuff that overestimated the central aortic pulse pressure by non-invasive method at "after NTG". FIG. 5 showed that the waveform signal data of combining the subjects with Baseline and After NTG, and the waveform signal data was analyzed by the Bland-Altman approach. FIG. 5(A) showed that in the Validation Group, it had the systematic bias via the non-invasive method to measure the central aortic pressure (PP-C) and via the cuff to measure the pulse pressure (Cuff-PP). The error was proportional to the PP-C value, and the standard deviation of difference was 12.4 mmHg.

In addition, FIG. 4 also showed that for the subjects at "Baseline", two kinds of values of the pulse pressure were estimated by a Generalized Transfer Function, such as $PP\text{-}C_{TFSBP\text{-}TFDBP}$ and $PP\text{-}C_{TFSBP\text{-}Cuff\ DBP}$, which still significantly underestimated the central aortic pulse pressure measured by the invasive method, and the scatter of difference (standard deviation of differences (SDD) between paired measurement) was quite larger. As shown in FIGS. 5(B) and 5(C), the Bland-Altman approach showed that $PP\text{-}C_{TFSBP\text{-}TFDBP}$ and $PP\text{-}C_{TFSBP\text{-}Cuff\ DBP}$ also exhibited the systematic bias proportionally, and the result for calculating the central aortic pulse pressure from the third method was quite similar, as shown in FIG. 5(D).

The Present Invention: An Improved Pulse Wave Analysis (PWA) Method for Estimating Central Aortic Pulse Pressure The present invention was related to an improved pulse wave analysis method that used the calibrated pressure pulse wave oscillation signal (non-invasively) obtained from the Generation Group to construct a multi-variate prediction model, and produced an equation for directly estimating the central aortic pulse pressure, in which the equation=−88.2+0.79*ESP+1.41*As +0.68*Ad−1.16*DBP+0.84*HR.

As shown in Table 1, variables were determined by Stepwise method and used to construct a best prediction model. The full model ($R^2$) was 0.88 (p<0.001), and the partial variation ($R^2$) of each variable was ESP=0.694, As=0.123, Ad=0.001, DBP=0.055 and heart rate=0.012 respectively. The mean difference and SDD (standard deviation of difference) at baseline and after NTG (0.6 mg) were −0.9±7.1 and 0.9±5.7 mmHg, respectively. On the other hand, the addition of the variables of such as age, sex, height, weight and waistline did not affect and improve the equation of the present invention. In addition, the variables did not show obvious systematic bias by the Bland-Altman analysis.

FIG. 6 showed that the accuracy of equation for predicting central aortic pulse pressure in the Generation Group and the Validation Group, respectively. FIG. 6(A) showed that in the Generation Group (40 subjects, 80 times of measurements), via the waveform analysis using the pulse volume plethysmography (PVP) and the prediction equation, the produced central aortic pulse pressure was capable of significantly decreasing the mean deviation (0 mmHg) and the standard deviation of difference (6.5 mmHg) of the central aortic pulse pressure measured by the invasive method obviously. In addition, FIG. 6(B) showed that in the Validation Group (100 subjects, 200 times of measurements), the prediction value of the central aortic pulse pressure calculated by the non-invasive method of the present invention still had higher accuracy (mean deviation=3 mmHg and the standard deviation of difference=7.1 mmHg). It did not exhibit obvious systematic bias via the Bland-Altman analysis.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those with skill in the art that, in light of the present disclosure, numerous modifications and changes can be made in the particular embodiments exemplified without departing from the intended scope of the invention. Moreover, due to biological functional equivalency considerations, changes can be made in protein structure without affecting the biological action in kind or amount. All such modifications are intended to be included within the scope of the appended claims.

TABLE 1

Multiple linear regression analysis of the non-invasive pulse wave analysis model for estimating PP-C directly (independent variable)

|  | Unstandardized regression coefficients | 95% CI | p-values | $R^2$ |
|---|---|---|---|---|
| Parameters included in the final model |  |  |  |  |
| ESP | 0.79 | 0.42~1.16 | <0.001 | 0.694 |
| As | 1.41 | 0.84~1.97 | <0.001 | 0.123 |
| Ad | 0.68 | 0.12~1.23 | 0.017 | 0.001 |
| DBP | −1.16 | −1.52~−0.81 | <0.001 | 0.055 |
| heart rate | 0.84 | 0.25~1.43 | 0.006 | 0.012 |
| All tested covariate in the model |  |  |  |  |
| SBP | 0.22 | −0.22~0.66 | 0.326 | 0.002 |
| MBP | −0.56 | −1.81~0.69 | 0.377 | 0.000 |
| DBP | −0.87 | −1.60~−0.14 | 0.020 | 0.059 |
| SBP2 | −0.16 | −0.62~0.30 | 0.478 | 0.005 |
| ESP | 1.00 | 0.35~1.66 | 0.003 | 0.511 |
| As | 1.47 | 0.77~2.17 | <0.001 | 0.202 |
| Ad | 0.64 | 0.05~1.24 | 0.035 | 0.030 |
| heart rate | 0.90 | 0.19~1.62 | 0.014 | 0.077 |

SBP2: secondary peak systolic pressure (SBP2) on peripheral pressure waveform
ESP: end-systolic pressure
Ad: area under the pressure tracing in diastole
As: area under the pressure tracing in diastole systole
SBP: systolic blood pressure
MBP: mean blood pressure
DBP: diastolic blood pressure

What is claimed is:

1. A novel sphygmomanometer for directly estimating central aortic pulse pressure by a pressure pulse wave oscillation signal of a cuff, comprising:
   (a) a control means for controlling a pressure of the cuff, which is used to control the proceeding of pressurization, maintenance and decompression in a measured location of the cuff;
   (b) at least one recording and storing means for recording and storing the pressure pulse wave oscillation signal of the cuff comprising a waveform of the pressure pulse wave oscillation signal of the cuff; and
   (c) a processing means for analyzing the recorded and stored waveform of the pressure pulse wave oscillation signal of the cuff to obtain values of a plurality of predicting variables, and calculating the central aortic pulse pressure in real time by substituting the values of the plurality of predicting variables into the following equation:

$a+b*ESP+c*As+d*Ad+e*DBP+f*HR,$ wherein
   A. the equation is stored in the at least one storing means, end-systolic pressure (ESP), area under a pressure tracing in systole (As), area under a pressure tracing in diastole (Ad), diastolic blood pressure (DBP) and heart rate (HR) are the plurality of predicting variables, and a is a constant and b, c, d, e and f are variable coefficients, and
   B. the equation is obtained by the following steps:
      (i) measuring a plurality of pressure pulse wave oscillation signals in the cuff, one or more brachial systolic blood pressures, and one or more diastolic blood pressures, wherein each pressure pulse wave oscillation signal comprises a waveform of the pressure pulse wave oscillation signal in the cuff;
      (ii) averaging the waveforms of the measured pressure pulse wave oscillation signals and calibrating an averaged waveform by using the systolic blood pressures and the diastolic blood pressures;
      (iii) analyzing the calibrated waveform of the pressure pulse wave oscillation signals to obtain a plurality of characteristic signal values serving as the plurality of predicting variables; and
      (iv) obtaining the constant a and the variable coefficients b, c, d, e, and f by linear regression analysis.

2. The device as claimed in claim 1, wherein the equation for estimating central aortic pulse pressure is: −88.2+0.79*ESP+1.41*As+0.68*Ad−1.16*DBP+0.84*HR.

3. The device as claimed in claim 1, wherein the central aortic pulse pressure is a pulse pressure at a carotid artery or an ascending aorta.

4. The device as claimed in claim 1, wherein the measured location is at a brachial artery.

5. The device as claimed in claim 1, wherein the at least one storing means is a chip or a memory storage device.

6. The device as claimed in claim 1, wherein the novel sphygmomanometer is capable of measuring systolic blood pressure (SBP) and diastolic blood pressure (DBP).

* * * * *